(12) United States Patent
Yokoyama et al.

(10) Patent No.: US 6,993,444 B2
(45) Date of Patent: Jan. 31, 2006

(54) MEASURING METHOD OF COMPONENT CONCENTRATION IN SOLUTION

(75) Inventors: Issei Yokoyama, Kyoto (JP); Yoshihito Yuhara, Kyoto (JP); Junji Kojima, Kyoto (JP); Takaaki Yada, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 10/932,860

(22) Filed: Sep. 2, 2004

(65) Prior Publication Data

US 2005/0065750 A1    Mar. 24, 2005

(30) Foreign Application Priority Data

Sep. 9, 2003   (JP)   ............... 2003-317131

(51) Int. Cl.
G01F 1/12    (2006.01)
G01J 5/02    (2006.01)

(52) U.S. Cl. ............................. 702/100; 250/339.12

(58) Field of Classification Search ............... 702/100, 702/135, 136, 137; 250/339.12, 339.11, 250/339.01, 339.03, 341.5; 356/301, 319
See application file for complete search history.

(56) References Cited

U.S. PATENT DOCUMENTS

| | | | | |
|---|---|---|---|---|
| 4,427,889 A | * | 1/1984 | Muller | 250/339.11 |
| 4,641,973 A | * | 2/1987 | Nestler et al. | 356/418 |
| 5,668,373 A | * | 9/1997 | Robbat et al. | 250/339.12 |
| 5,696,580 A | * | 12/1997 | Kubo et al. | 356/72 |
| 5,729,342 A | * | 3/1998 | Yokoyama et al. | 356/319 |
| 5,796,476 A | * | 8/1998 | Wang et al. | 356/301 |
| 5,886,347 A | * | 3/1999 | Inoue et al. | 250/339.12 |
| 2003/0052272 A1 | | 3/2003 | Kiuchi et al. | 250/339.12 |

FOREIGN PATENT DOCUMENTS

| | | |
|---|---|---|
| EP | 0 418 799 A2 | 3/1991 |
| EP | 0 418 799 A3 | 3/1991 |
| EP | 0 559 305 A2 | 9/1993 |
| EP | 0 559 305 A3 | 9/1993 |
| JP | 10030982 | 2/1998 |
| JP | 2001-066251 | 3/2001 |
| JP | 2003-121352 | 4/2003 |

* cited by examiner

Primary Examiner—Bryan Bui
Assistant Examiner—Toan M. Le

(57) ABSTRACT

A measuring method of determining component concentration in a solution by calculating component concentrations in the solution at various temperatures in a small number of steps. The component concentration is measured at an arbitrary temperature T by using a solution absorbance spectrum and solvent absorbance spectrum at a plurality of wavelength(s)r, and preliminarily determining a calibration coefficient $M_{ij}(T_O)$. Concentration of $C_i$ of component i in solution at reference temperature $T_O$, is obtained at differential spectrum of solution spectrum $S(\lambda_j, T)$ at temperature T in j-th wavelength $\lambda_j$ and solvent spectrum $B(\lambda_j, T)$ at temperature T in j-th wavelength $\lambda_j$, calculating calibration coefficient $M_{ij}(T_O)$ the specific component concentrations.

4 Claims, 5 Drawing Sheets

MEASURING METHOD OF COMPONENT CONCENTRATION IN SOLUTION

BACKGROUND OF THE INVENTION

1. Field of the Invention

The present invention relates to a measuring method of determining component concentrations in a solution including an efficient determination of a calibration coefficient from a solution spectrum and solvent spectrum to enable measurement.

2. Description of the Prior Art

It is necessary in various industrial and scientific fields to accurately measure the components in a sample or in a production environment. For example, in manufacturing semiconductor components high accuracy is required and the concentration of components in any chemical solution used must be carefully controlled in the production process. Additionally, temperature can also have an impact and will effect the measurement calculations. For example, to calculate component concentrations in a fluid solution at various temperatures, heretofor, calibration coefficients $M_{ij}(T_1)$, $M_{ij}(T_2)$, ... $M_{ij}(T_k)$ at a plurality of different temperatures $T_1$, $T_2$, ... $T_k$ had to be determined, and at T=about $T_k$, the component concentration in solution $C_i(T)$ was calculated by the following formula:

$$C_i(T) = \sum_{j=1}^{m} m_{ij}(T_k)S(\lambda_j, T) + M_{i0}(T_k) \tag{1}$$

In formula (1), i denotes a component, $\lambda_j$ denotes j-th wavelength, and $S(\lambda_j, T)$ denotes the solution spectrum at arbitrary temperature T in j-th wavelength $\lambda_j$.

As can be determined a significant number of technical steps had to be performed by a skilled technician to obtain a large number of calibration coefficients.

Thus, there is a need for improving the ability to efficient control the measurement of components in a fluid solution.

SUMMARY OF THE INVENTION

An object of the present invention is to provide a measuring method of determining the amount of component concentration in a fluid solution by at various temperatures in a small number of steps. To achieve this object, a measuring method measures the component concentration in solution at an arbitrary temperature T by using a solution spectrum and solvent spectrum at each wavelength, a preliminarily determination of the calibration coefficient $M_{ij}(T_O)$ for measuring concentration $C_i$ of component i in solution at reference temperature $T_O$, is obtained from a differential spectrum of solution spectrum $S(\lambda_j, T)$ at temperature T in j-th wavelength $\lambda_j$ and solvent spectrum $B(\lambda_j, T)$ at temperature in j-th wavelength $\lambda_j$, for calculating the calibration coefficient $M_{ij}(T_O)$.

In the invention, the solvent spectrum $B(\lambda_j, T)$ is preferred to be expressed as $$B(\lambda_j, T) = \sum_{i=1}^{n} k_i(\lambda_j)(T - T_0)^i$$

wherein $k_i(\lambda_j)$: coefficient of degree of i about temperature in j-th wavelength $\lambda_j$.

By calculating the differential spectrum of solution spectrum $S(\lambda_j, T)$ at temperature T in j-th wavelength $\lambda_j$ and solvent spectrum $B(\lambda_j, T)$ at temperature T in j-th wavelength $\lambda_j$, with the calibration coefficient $M_{ij}(T_O)$ for measurement of concentration $C_i$ of component i in the solution at reference temperature $T_O$ determined preliminarily, the concentration of component i in the solution can be calculated. That is, in the invention, solution spectrum $S(\lambda_j, T)$ and solvent spectrum $B(\lambda_j, T)$ at various temperatures T can be determined as measured physical quantities, and instead of using plural calibration coefficients $M_{ij}(T_1)$, $M_{ij}(T_2)$, ... $M_{ij}(T_k)$ at plural temperatures $T_1$, $T_2$, ... $T_k$ as in the conventional method, by using only one calibration coefficient $M_{ij}(T_O)$(i is component in solution, and j is wavelength point) at reference temperature $T_O$, components concentration in solution at various temperatures can be accurately calculated. This invention requires only one calibration coefficient and since a determination of a calibration calculation takes most of the time and labor, the number of steps for acquiring the calibration coefficients is saved.

Also in the invention, the solvent spectrum $B(\lambda_j, T)$ at temperature T in j-th wavelength $\lambda_j$ is expressed as $$B(\lambda_j, T) = \sum_{i=1}^{n} k_i(\lambda_j)(T - T_0)^i$$

wherein $k_i(\lambda_j)$: coefficient of degree of i about temperature in j-th wave length $\lambda_j$, and $B(\lambda_j, T)$ is used by defining the n-th degree function of $(T-T_O)$.

For example, the invention can be applied in support of concentration management in a one-bath apparatus (see FIG. 4) for keeping constant the concentration of a chemical solution at a high temperature (for example, 65° C. or 75° C.) so that it can be used in removal of particles in a cleaning process of wafers or the like in semiconductor manufacturing. As shown in FIG. 4, a chemical solution at a high temperature (for example, an aqueous solution of ammonia and hydrogen peroxide: $NH_3/H_2O_2/H_2O$) is directly supplied into a flow cell by a circulation pump, and the concentration of components ($NH_3$, $H_2O_2$, $H_2O$) of the chemical solution are constantly monitored so that the concentration of the chemical solution may be kept within an allowable range (concentration measuring range of $NH_3$: for example, 0.00 to 1.00%, concentration measuring range of $H_2O_2$: for example, 0.0 to 5.00%, concentration measuring range of $H_2O$: for example, 94.0 to 100.0%), and measurement results of the monitoring of concentration must be fed back to keep constant the concentration. In this case, for optimum feedback control depending on the concentration changes of the chemical solution, a quick measuring response of a concentration monitor is required, and by preliminarily measuring and storing $$B(\lambda_j, T) = \sum_{i=1}^{n} k_i(\lambda_j)(T - T_0)^i$$

a quick measuring response is realized when monitoring the concentration, and the follow-up performance depending on concentration changes of the chemical solution can be enhanced.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention.

Preferred embodiments of the present invention are described below by referring to the accompanying drawings. It must be noted, however, that the invention should not be limited by the illustrated preferred embodiments.

In a measuring method of determining component concentration in a solution, first calibration coefficient $M_{ij}(T_O)$ is determined preliminarily to measure the concentration $C_i$ of component i in the solution at a reference temperature $T_O$ (for example, 25° C.). At this time, $$C_i(T_o) = \Sigma M_{ij}(T_o) S(\lambda_j, T_o) + M_{io}(T_o)$$

$$C_i(T_o) = \Sigma M_{ij}(T_o) S(\lambda_j, T_o) + M_{io}(T_o). \quad (2)$$

wherein $S(\lambda_j, T_O)$ indicates the solution spectrum (absorbance spectrum, etc.) at reference temperature $T_O$ in j-th wavelength $\lambda_j$, and $M_{io}(T_O)$ is a constant not depending on the solution spectrum $S(\lambda_j, T_O)$, and relating to component i at the reference temperature $T_O$.

Suppose the solvent spectrum of solvent (for example, $H_2O$) as a principal component of the solution at a temperature T in j-th wavelength $\lambda_j$ to be B $(\lambda_j, T)$. At this time, it is defined so that the solvent spectrum B $(\lambda_j, T_O)$ at reference temperature $T_O$ in j-th wavelength $\lambda_j$ may be zero in all wavelengths (the reference is shifted). That is, $$B(\lambda_j, T_o) = 0 \quad (3)$$

Figure 1:
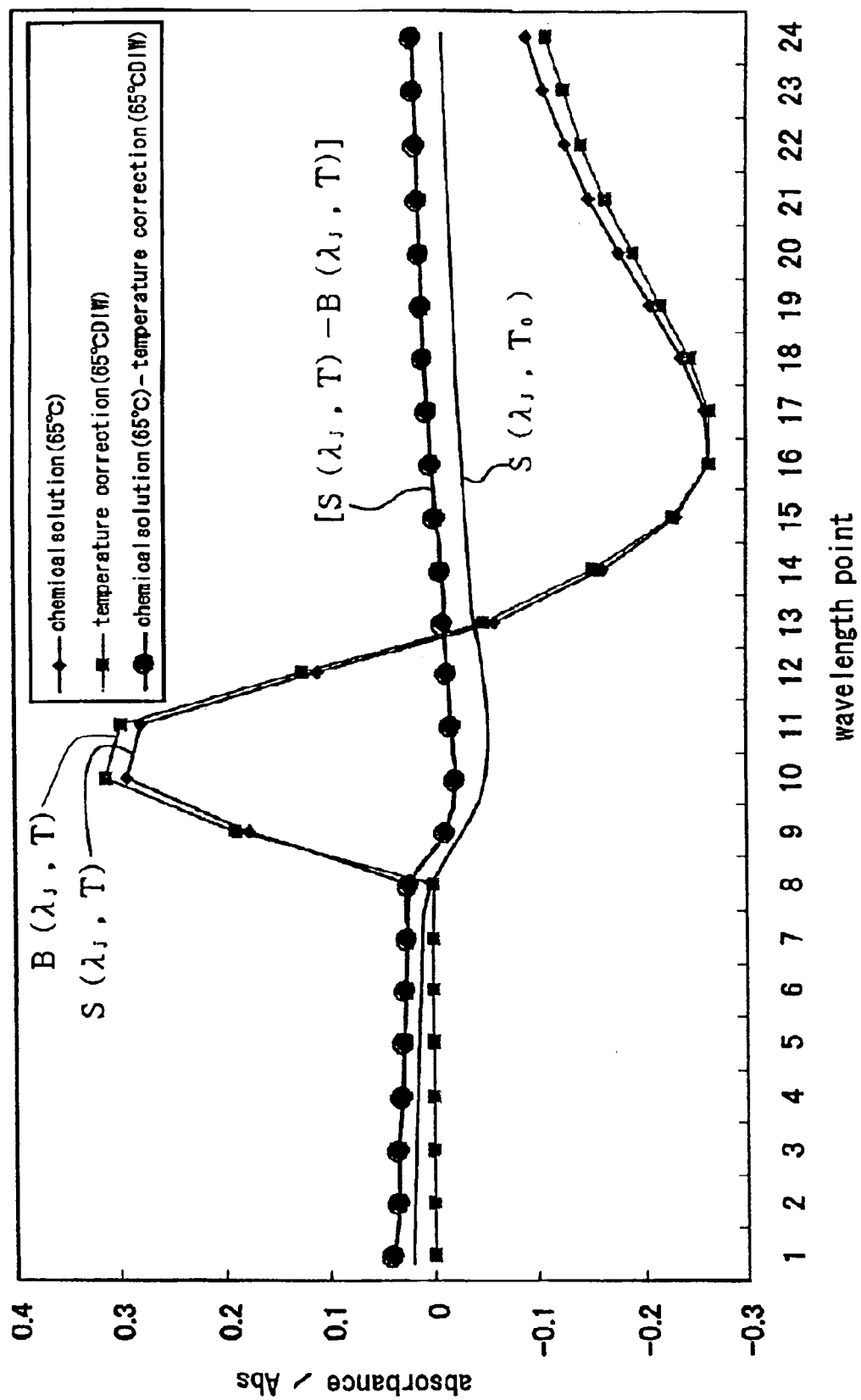
FIG. 1 is a characteristic diagram used for the explanation of the calculation of a temperature correction in a preferred embodiment of the invention.

At this time, as shown in FIG. 1, the differential spectrum of solution spectrum S $(\lambda_j, T)$ at temperature T in j-th wavelength $\lambda_j$ and solvent spectrum B $(\lambda_j, T)$ at temperature T in j-th wavelength $\lambda_j$ (see FIG. 1) is, when the solvent concentration is high, for example, 95% or more, approximately equal to the difference between the solution spectrum S $(\lambda_j, T_O)$ at reference temperature $T_O$ in j-th wavelength $\lambda_j$ and solvent spectrum B $(\lambda_j, T_O)$ at reference temperature $T_O$ in j-th wavelength $\lambda_j$, as known from the experiment by the present inventors. That is, $$S(\lambda_j, T) - B(\lambda_j, T) = S(\lambda_j, T_o) - B(\lambda_j, T_o) = S(\lambda_j, T_o) \quad (4)$$

Therefore, putting $S(\lambda_j, T_O)$ in formula (2) into formula (4), and replacing $C_i(T_O)$ in formula (2) with $C_i(T)$, the component concentration at temperature T after temperature correction can be expressed in the following formula.

$$C_i(T) = \sum_{j=1}^{m} M_{ij}(T_o)[S(\lambda_j, T) - B(\lambda_j, T)] + M_{io}(T_o) \quad (5)$$

Accordingly, the present inventors have provided an equation which can be implemented in a control system, for example, with the assistance of a computer to enable a constant monitoring of the components in a fluid solution with adjustments for temperature correction. The empirical derivation of this improvement verified the relationships and led the present inventors to simplifying the determination of a relevant calibration coefficient to enable an efficient and accurate determination of components in a fluid solution.

In the embodiment shown in FIG. 1, the chemical solution at the same temperature (65° C.) as when using $H_2O$ at 65° C. as solvent is used as the solution.

From formula (5), it is possible by only determining the calibration coefficient $M_{ij}(T_O)$ of solution at reference temperature $T_O$, and solution spectrum S $(\lambda_j, T)$ and solvent spectrum B $(\lambda_j, T)$ at various temperatures, for the component concentrations in the solution to be calculated, and only one calibration coefficient consuming time step in calculation is enough, and a number of preparatory measurement steps can be saved.

FIG. 2 shows the temperature correction effect of the invention, by recording the measurement results of an application of the invention, for example, in calculation of concentration of components ($NH_3$, $H_2O_2$, $H_2O$) of the chemical solution at a high temperature (for example, an aqueous solution of ammonia and hydrogen peroxide) used in wafer cleaning. In this example, the chemical solution at the same temperature (75° C.) as when using $H_2O$ at 75° C. as solvent is used as the solution.

Figure 2A:
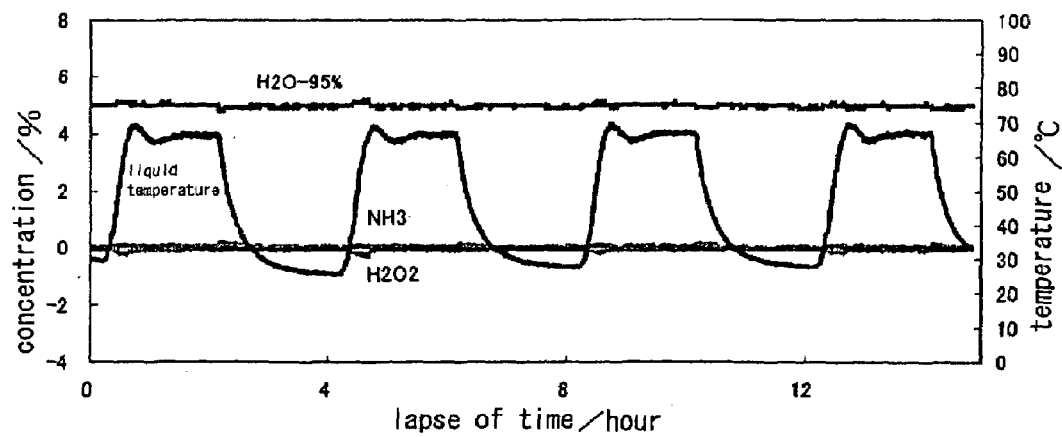
FIG. 2A is a diagram showing measurement results with temperature correction in the preferred embodiment.
Figure 2B:
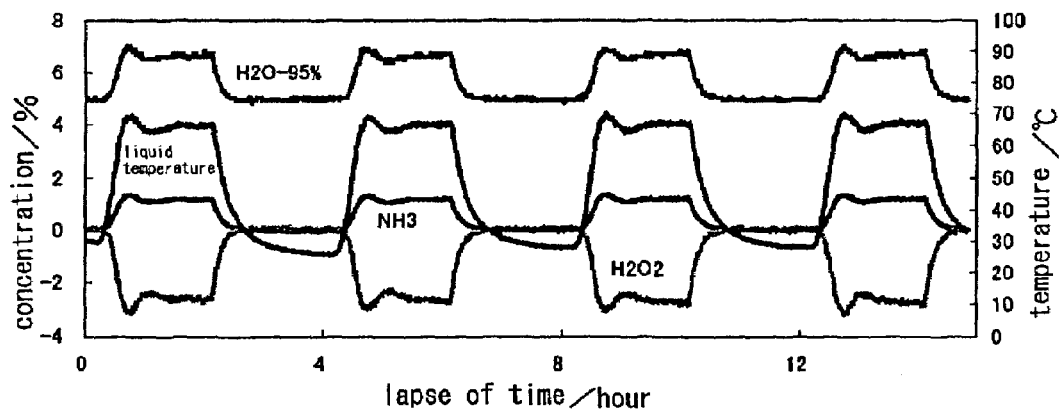
FIG. 2B is a diagram showing measurement results without temperature correction.

FIG. 2A shows the measurement results obtained from formula (5) of the invention by temperature correction. FIG. 2B shows measurement results in a comparative example without temperature correction, and the result is calculated directly from formula (2) without putting formula (4) into S ($\lambda_j$, $T_O$) in formula (2).

As known from FIG. 2A, the chemical solution at high temperature contains almost only $H_2O$ at 75° C. In FIG. 2B, although $NH_3$ and $H_2O_2$ are not actually contained, the concentration and temperature of these components and $H_2O$ vary with the lapse of time.

Figure 3A:
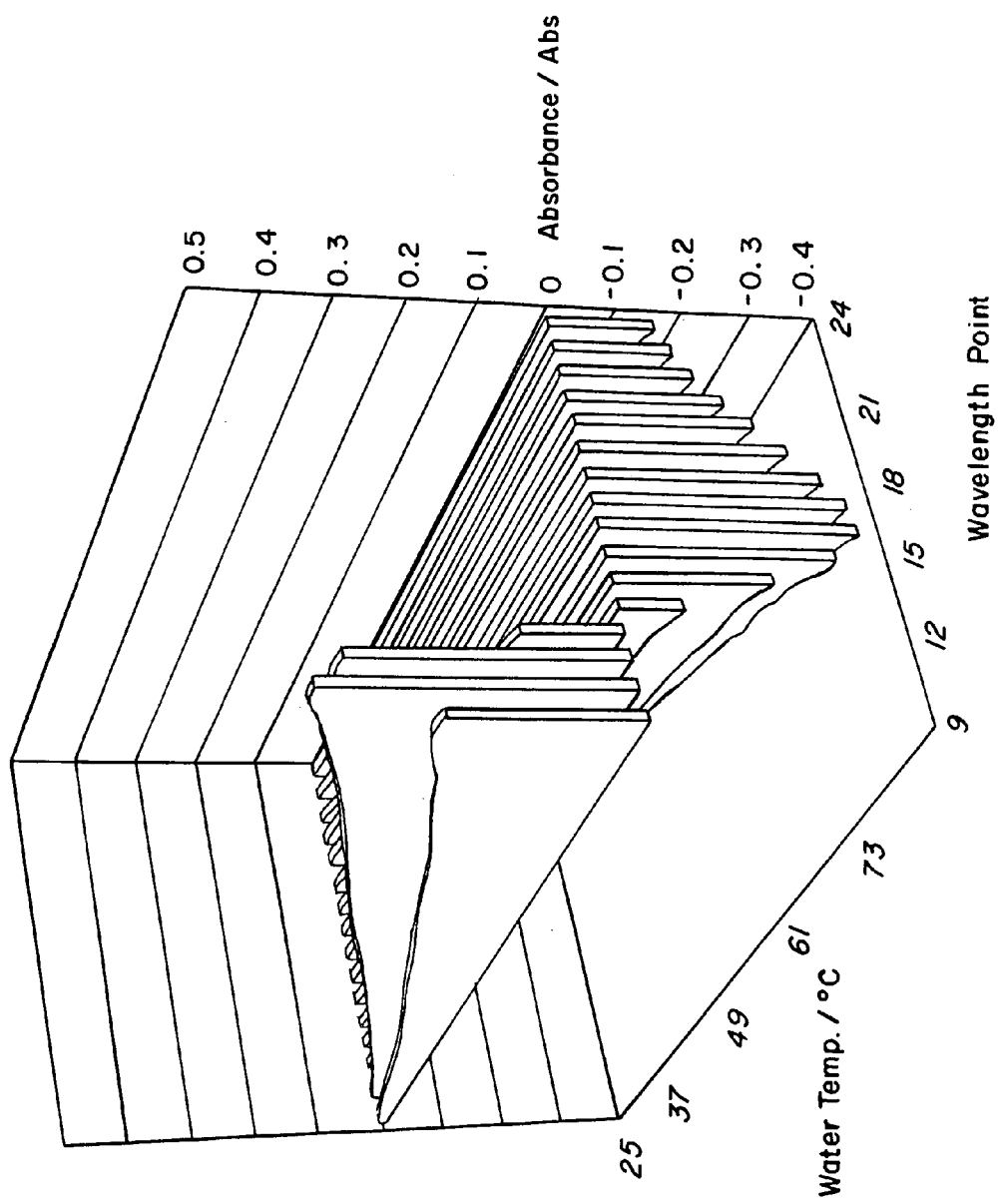
FIG. 3A is a three-dimensional graph by water temperature, wavelength point, and absorbance in the case of solvent spectrum B $(\lambda_j, T)$ expressed by the quadratic function of $(T-T_O)$ in the preferred embodiment.
Figure 3B:
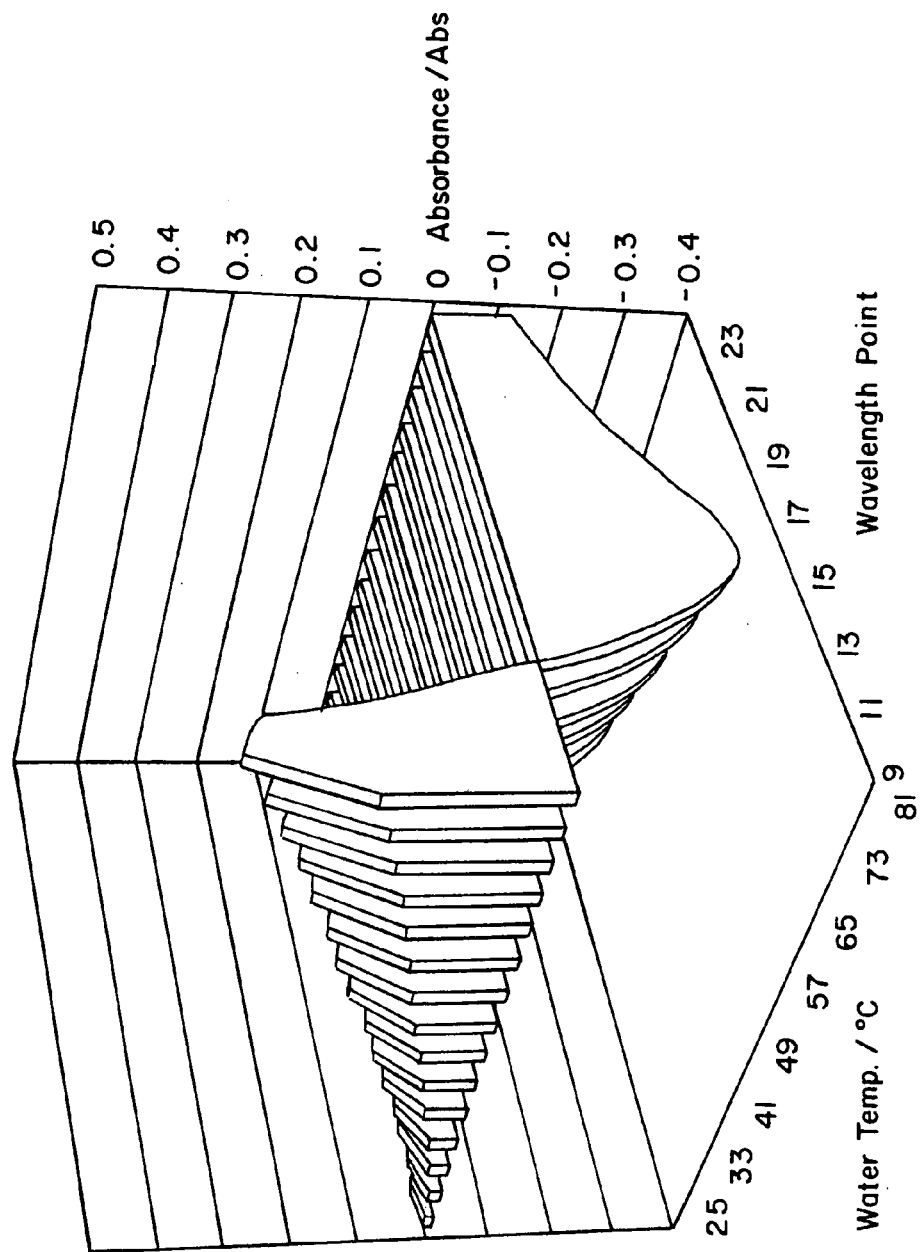
FIG. 3B is a three-dimensional graph by water temperature, wavelength point, and absorbance as seen from other aspect in the case of solvent spectrum B $(\lambda_j, T)$ expressed by the quadratic function of $(T-T_O)$ in the preferred embodiment.

FIG. 3 shows three-dimensional graphs by water temperature, wavelength point, and absorbance in the case of solvent spectrum B ($\lambda_j$, T) expressed by quadratic function of (T-$T_O$). FIG. 3A and FIG. 3B shows different aspects of the same data.

Figure 4:
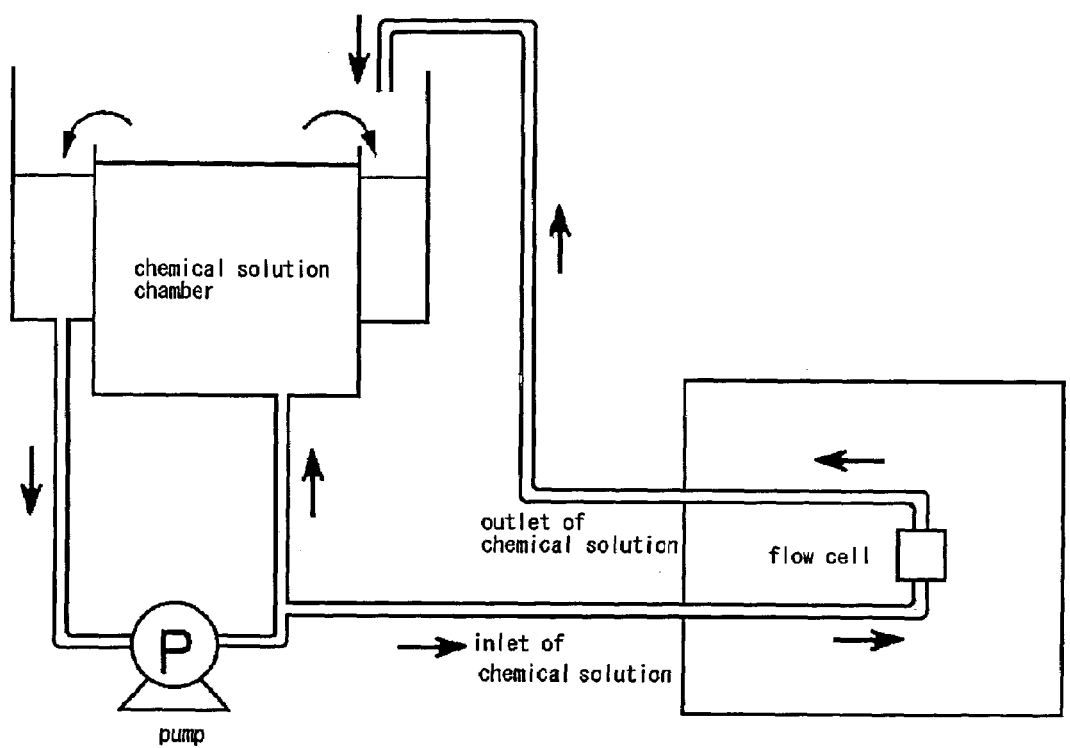
FIG. 4 is a schematic explanatory diagram of a one-bath apparatus according to the preferred embodiment.

Referring to FIG. 4, the chemical solution cleansing bath is one example of the use of the present invention. Initially, a single calibration coefficient is derived at a reference temperature $T_o$ by measurements in the flow cell over a predetermined applicable range of wavelength permits applicable to the specific components so that an absorbance spectrum for both the solution spectrum and the components is determined. Equation 2 is used to establish the calibration coefficient $M_{ij}(T_o)$. This reference temperature and calibration coefficient can be stored and accessed by a program executed by a computer.

To monitor the cleansing bath, measurements of the temperature of the bath are periodically taken and the component concentration is also measured at the flow cell over a predetermined range of wavelengths to determine absorbance for each wavelength point. Theses values can be used with the calibration coefficient in accordance with Equitation 5 to determine the specific level of concentrations adjusted by the current temperature of the bath.

Thus, it is possible to monitor and when necessary to adjust the ratio of components in the bath to maintain an optimum level.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. A measuring method of determining component concentration in a solution, which measures the component concentration in solution at an arbitrary temperature T by using a solution spectrum and solvent spectrum at each wavelength, characterized by preliminarily determining a calibration coefficient $M_{ij}(T_O)$ for measuring concentration $C_i$ of component i in the solution at a reference temperature $T_O$, comprising the steps of:

obtaining a differential spectrum of solution spectrum S ($\lambda_j$, T) at temperature T in j-th wavelength $\lambda_j$ and solvent spectrum B ($\lambda_j$, T) at temperature T in j-th wavelength $\lambda_j$, and calculating the calibration coefficient $M_{ij}$ ($T_O$) from the differential spectrums.

2. A measuring method of component concentration in solution according to claim 1, wherein the solvent spectrum B ($\lambda_j$, T) is preferred to be expressed as $$B(\lambda_j, T) = \sum_{i=1}^{n} k_i(\lambda_j) \times (T - T_0)^i$$

wherein $k_i(\lambda_j)$: coefficient of degree of i about temperature in j-th wavelength $\lambda_j$.

3. A method of measuring component concentrations in a fluid solution comprising:

determining only a single calibration coefficient at a reference temperature for the component to be measured;

measuring the absorbance of the solution spectrum across a predetermined wavelength range that is subject to absorbance by the component at a predetermined temperature;

measuring the absorbance of the solvent spectrum across the predetermined wavelength range at the predetermined temperature; and determining from only the single calibration coefficient, and the differences between the measured solution spectrum and the measured solvent spectrum adjusted for the difference between the reference temperature and the predetermined temperature the component concentrations.

4. A method of adjusting a component concentration in a fluid solution, comprising the steps of:

determining a calibration coefficient at a reference temperature by measuring a solution spectrum across a predetermined wavelength range for a predetermined amount of the component concentration;

measuring a temperature of the fluid solution;

measuring the absorbance of the component across the predetermined wavelength range, determining from only the calibration coefficient, the measured temperature and the measured absorbance of the component across the predetermined wavelength range a component concentration; and adjust the determined component concentration in the fluid solution to match the predetermined amount of component concentration.

* * * * *